United States Patent
Czupi et al.

(10) Patent No.: US 12,064,294 B2
(45) Date of Patent: Aug. 20, 2024

(54) PROBE HOLDER ILLUMINATION FOR ULTRASOUND IMAGING SYSTEMS

(71) Applicant: GE Precision Healthcare LLC, Wauwatosa, WI (US)

(72) Inventors: Balint Czupi, Seewalchen am Attersee (AT); Markus Paarhammer, Oberwang (AT)

(73) Assignee: GE Precision Healthcare LLC, Wauwatosa, WI (US)

( * ) Notice: Subject to any disclaimer, the term of this patent is extended or adjusted under 35 U.S.C. 154(b) by 87 days.

(21) Appl. No.: 17/137,630

(22) Filed: Dec. 30, 2020

(65) Prior Publication Data

US 2022/0202522 A1  Jun. 30, 2022

(51) Int. Cl.
  *A61B 8/00* (2006.01)
  *A61B 90/30* (2016.01)
  *A61B 90/92* (2016.01)
  *G08B 5/36* (2006.01)
  *G08B 21/18* (2006.01)

(52) U.S. Cl.
  CPC ............ *A61B 90/30* (2016.02); *A61B 8/4433* (2013.01); *A61B 8/4444* (2013.01); *A61B 8/4477* (2013.01); *A61B 8/58* (2013.01); *A61B 90/92* (2016.02); *G08B 5/36* (2013.01); *G08B 21/18* (2013.01); *A61B 8/4472* (2013.01)

(58) Field of Classification Search
  CPC ..... A61B 90/30; A61B 8/4433; A61B 8/4444; A61B 8/4477; A61B 8/58; A61B 90/92; A61B 8/4472; A61B 2090/0811; A61B 8/4405; A61B 8/54; A61B 8/46; A61B 2090/0807; A61B 2090/378; G08B 5/36; G08B 21/18

See application file for complete search history.

(56) References Cited

U.S. PATENT DOCUMENTS

| | | | |
|---|---|---|---|
| 2003/0236463 A1* | 12/2003 | Mesaros | A61B 8/00 600/459 |
| 2010/0204617 A1* | 8/2010 | Ben-Ezra | A61N 7/02 600/459 |
| 2013/0211221 A1* | 8/2013 | Sunnarborg | A61B 5/742 600/373 |
| 2017/0150944 A1* | 6/2017 | Kim | A61B 8/00 |
| 2019/0307423 A1* | 10/2019 | Han | A61B 8/44 |
| 2020/0000430 A1* | 1/2020 | Chamberlain | A61B 8/12 |
| 2021/0010991 A1* | 1/2021 | McLeod | G01N 33/1893 |
| 2021/0059636 A1* | 3/2021 | Durfee | A61B 8/0841 |
| 2021/0349211 A1* | 11/2021 | Halmann | A61B 8/463 |

OTHER PUBLICATIONS

U.S. Appl. No. 16/862,206, filed Apr. 29, 2020, GE Precision Healthcare LLC.

* cited by examiner

Primary Examiner — Alexei Bykhovski (57) ABSTRACT

A method and ultrasound imaging system including a plurality of probe holders and a plurality of light assemblies attached to the plurality of probe holders. The plurality of light assemblies is configured to be controlled by a processor to selectively illuminate one or more of the plurality of probe holders.

18 Claims, 6 Drawing Sheets

PROBE HOLDER ILLUMINATION FOR ULTRASOUND IMAGING SYSTEMS

FIELD OF THE INVENTION

This disclosure relates generally to an ultrasound imaging system and method for controlling a plurality of light assemblies in order to selectively illuminate one or more a plurality of probe holders that are part of the ultrasound imaging system.

BACKGROUND OF THE INVENTION

Ultrasound examinations are typically performed in rooms with the lights either dimmed down significantly or turned off to make it easier for the clinician to clearly see details in the images acquired by the ultrasound imaging system. The ultrasound probes are typically stored in probe holders along the sides of the ultrasound imaging system. Very little light from the display or the user interface reaches the probe holders. As a result, it can be difficult for a clinician to quickly and efficiently select the desired ultrasound probe for a given ultrasound protocol. Additionally, after using the ultrasound probe to perform the ultrasound examination, it can be difficult for the clinician to locate the appropriate probe holder for storing the ultrasound probe after the examination using conventional ultrasound imaging systems.

Additionally, some ultrasound imaging systems use sensors associated with each probe holder to detect when an ultrasound probe is in the probe holder and when the ultrasound probe associated with a particular probe holder is in use. For some of these ultrasound imaging systems it is important to make sure that each ultrasound probe is returned to its associated probe holder. Due to the low-light environment, it can be difficult for clinicians to locate the associated probe holder after performing an examination.

For at least the reasons discussed hereinabove, there is a need for an improved ultrasound imaging system and method for use with an ultrasound imaging system.

BRIEF DESCRIPTION OF THE INVENTION

The above-mentioned shortcomings, disadvantages, and problems are addressed herein which will be understood by reading and understanding the following specification.

In accordance with an embodiment, an ultrasound imaging system includes a plurality of probe holders. The ultrasound imaging system includes a plurality of light assemblies attached to the plurality of probe holders, wherein each of the plurality of light assemblies is configured to selectively illuminate a different one of the plurality of probe holders. The ultrasound imaging system includes a processor connected to the plurality of light assemblies, wherein the processor is configured to control the plurality of light assemblies in order to selectively illuminate one or more of the plurality of probe holders.

In accordance with an embodiment, a method for use with an ultrasound imaging system including a plurality of probe holders and a plurality of ultrasound probes, where each of the plurality of ultrasound probes is associated with a different one of the plurality of probe holders, and a plurality of light assemblies attached to the plurality of probe holders. The method includes receiving a probe status with respect to one of the plurality of ultrasound probes and controlling, with a processor, the plurality of probe holders associated with the one of the plurality of ultrasound probes in order to convey the probe status.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized, and logical, mechanical, electrical and other changes may be made without departing from the scope of the embodiments. The following detailed description is, therefore, not to be taken as limiting the scope of the invention.

Figure 1:
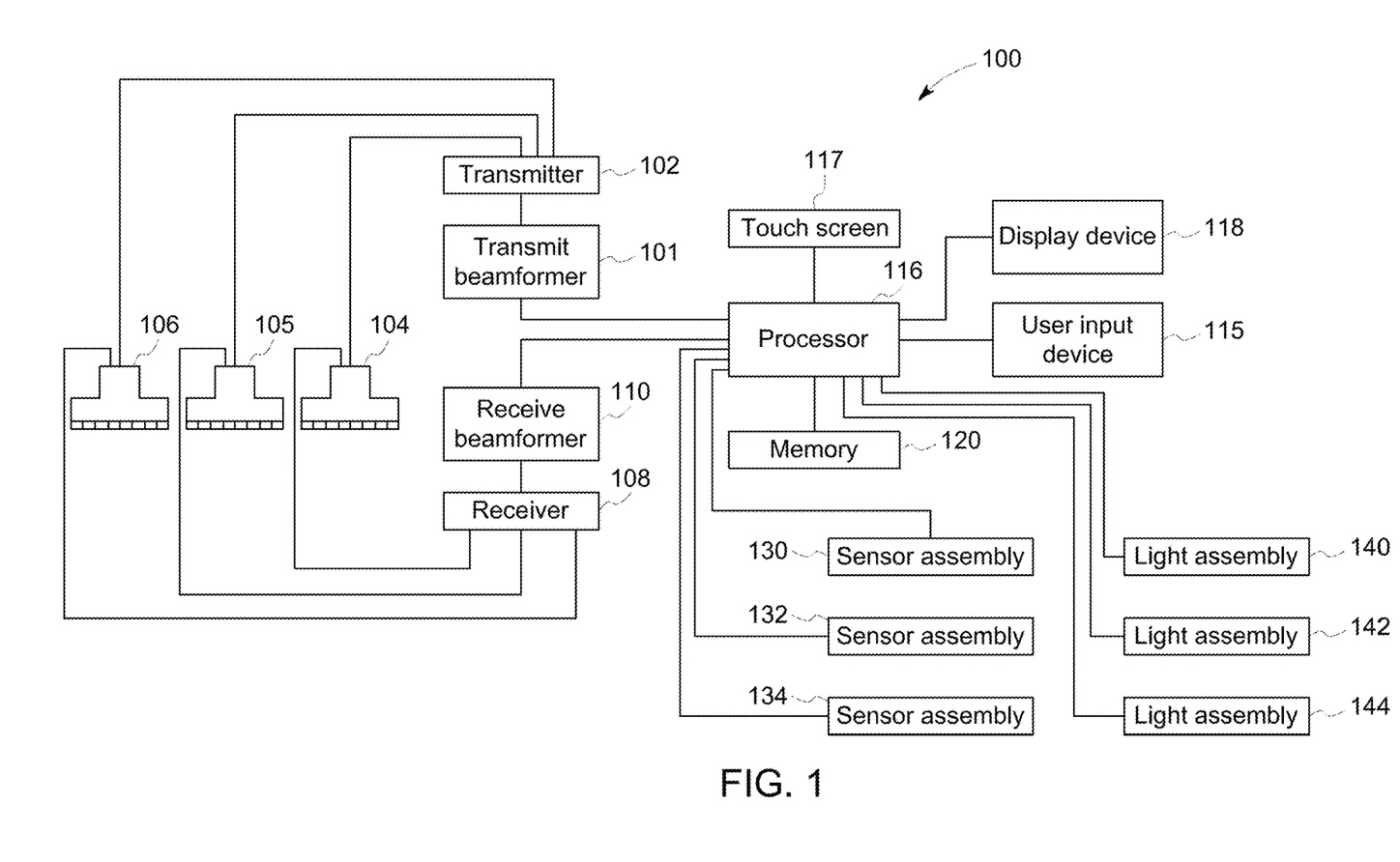
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a first ultrasound probe 104, a second ultrasound probe 105, and a third ultrasound probe 106 in accordance with an exemplary embodiment. Other embodiments may have only a single ultrasound probe, two ultrasound probes or more than three ultrasound probes. The ultrasound imaging system 100 includes a transmit beamformer 101 and a transmitter 102 that drive elements within one of the ultrasound probes (104, 105, 106). For example, if the first ultrasound probe 104 is active, the transmit beamformer 101 and the transmitter 102 may be used to drive elements within the first ultrasound probe 104. Each of the ultrasound probes (104, 105, 106) may be a linear probe, a curved linear probe, a 2D array, a mechanical 3D/4D probe, an E4D probe capable of full beamforming in both elevation and azimuth directions, or any other type of ultrasound probe capable of acquiring ultrasound data. FIG. 1 will be described according to an embodiment where the first ultrasound probe 104 is active, but it should be appreciated that the second ultrasound probe 105 or the third ultrasound probe 106 may be active and used to acquired ultrasound data by selecting either the second ultrasound probe 105 or the third ultrasound probe 106.

Still referring to FIG. 1, the pulsed ultrasonic signals are back-scattered from structures in the body, like blood cells or muscular tissue, to produce echoes that return to the elements of the first probe 104. The echoes are converted into electrical signals by the elements 104, and the electrical signals are received by a receiver 108. The electrical signals representing the received echoes are passed through a receive beamformer 110 that outputs ultrasound data. According to some embodiments, the first ultrasound probe 104 may contain electronic circuitry to do all or part of the transmit and/or the receive beamforming. For example, all or part of the transmit beamformer 101, the transmitter 102, the receiver 108, and the receive beamformer 110 may be situated within one or more of the ultrasound probes (104, 105, 106). The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user input device 115 may be used to control operation of the ultrasound imaging system 100, including to control the input of patient data, to change a scanning or ultrasound parameter, and the like.

The ultrasound imaging system 100 also includes a processor 116 to control the transmit beamformer 101, the transmitter 102, the receiver 108, and the receive beamformer 110. The processor 116 is in electronic communication with the ultrasound probes (104, 105, 106). The processor 116 may control any one of the three ultrasound probes to acquire ultrasound data. The processor 116 controls which of the elements in the selected ultrasound probe are active and the shape of a beam emitted from the selected ultrasound probe. The ultrasound imaging system 100 may also include a touch screen 117 according to an embodiment. The touch screen 117 provides and input/output interface between the ultrasound imaging system 100 and a user. The processor 116 sends signals to the touch screen 117, causing the touch screen 117 to display visual outputs to the user, such as images, a graphical user interface (GUI), video clips, menus, or any other type of visual output. The touch screen 117 outputs signals to the processor 116 based on the touch inputs, which may be in the form of one or more touch gestures, received via the touch screen 117.

The touch screen 117 includes a touch-sensitive surface or layer configured to receive touch inputs from the user. The touch screen 117 in combination with the processor 116 converts one or more detected touch gestures into actions, commands, or interactions. In some embodiments, the touch gestures may interact with a GUI displayed on the touch screen 117. The user may interact with the touch screen 117 using one or more fingers and/or an object, such as a stylus.

The touch screen 117 may use any type of technology to display visual outputs including a light-emitting diode (LED) display, an organic light-emitting diode (OLED) display, a liquid crystal display (LCD), a variable graphics array (VGA), or any other type of apparatus configured for displaying an image. Other display technologies may be used in other embodiments.

The ultrasound imaging system 100 includes a display device 118 in electronic communication with the processor 116. The display device 118 may use any type of technology to display visual outputs including a light-emitting diode (LED) display, an organic light-emitting diode (OLED) display, a liquid crystal display (LCD), a variable graphics array (VGA), or any other type of apparatus configured for displaying an image. The display device 118 may also be configured to display graphical user interface (GUI) elements.

For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, an FPGA, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For purposes of this disclosure, the term "real-time" will be additionally defined to include an action occurring within 2 seconds. For example, if data is acquired, then a real-time display of that data would occur within 2 seconds. Those skilled in the art will appreciate that most real-time procedures or processes will be performed in substantially less time than 2 seconds. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a given frame-rate or volume-rate. Images generated from the data may be refreshed at a similar frame-rate or volume-rate. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

Figure 2:
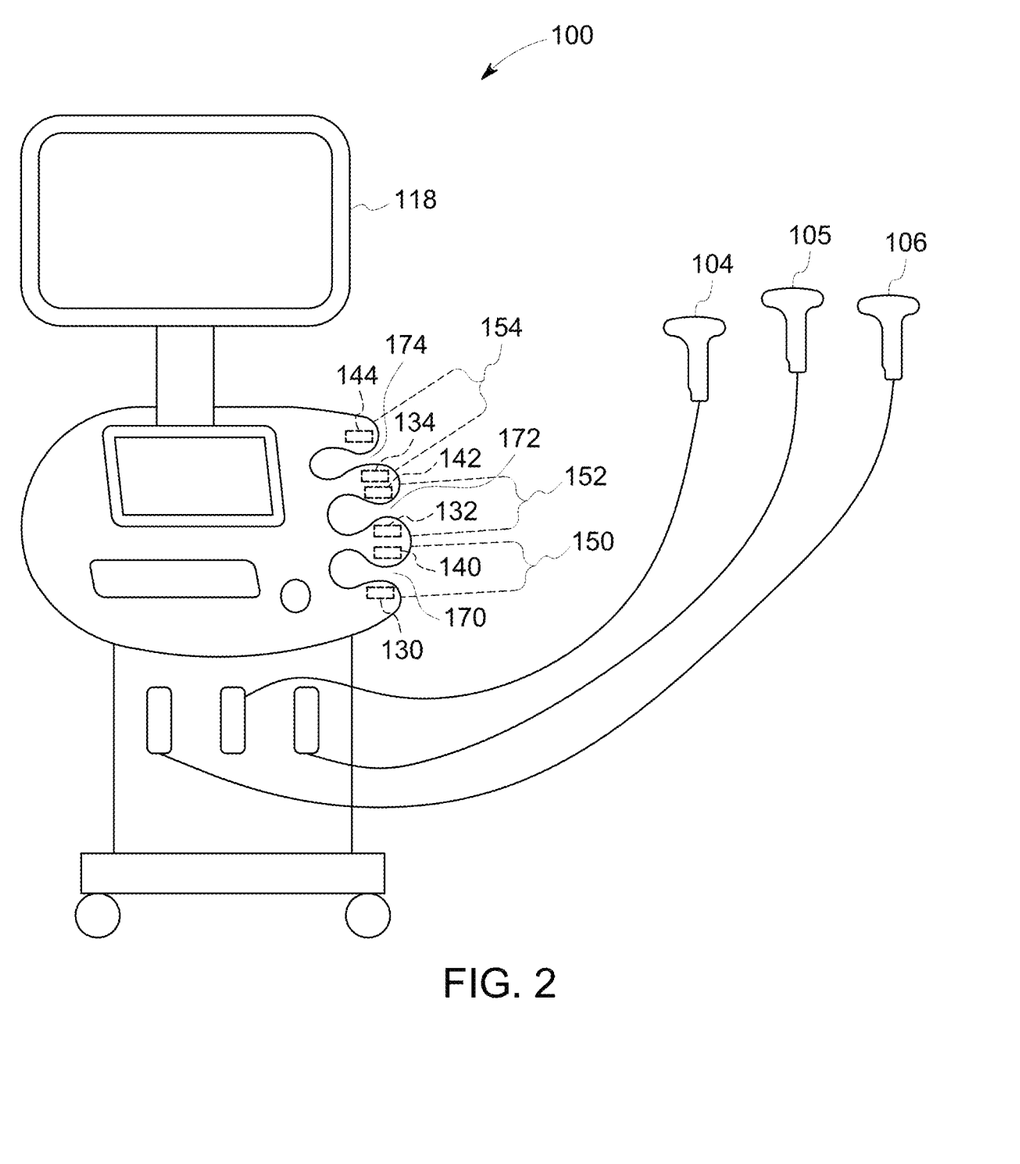
FIG. 2 is an illustration of an ultrasound imaging system in accordance with an embodiment.

FIG. 2 is an illustration of the ultrasound imaging system 100 in accordance with an exemplary embodiment. The ultrasound imaging system 100 includes a plurality of sensor assemblies and a plurality of light assemblies. The ultrasound imaging system 100 includes a first sensor assembly 130, a second sensor assembly 132, and a third sensor assembly 134. The ultrasound imaging system 100 includes a first light assembly 140, a second light assembly 142, and a third light assembly 144. The first sensor assembly 130, the second sensor assembly 132, and the third sensor assembly 134 are each in electronic communication with the processor 116. The first light assembly 140, the second light assembly 142, and the third light assembly 144 are each in electronic communication with the processor 116. The ultrasound imaging system 100 shown in FIG. 1 includes three sensor assemblies and three light assemblies. However, other embodiments may have a different number of sensor assemblies and/or a different number of light assemblies.

The ultrasound imaging system 100 includes a plurality of probe holders: a first probe holder 150, a second probe holder 152, and a third probe holder 154. Each of the probe holders (150, 152, 154) defines a slot for allowing passage of a cable of the ultrasound probe according to an embodiment. For example, the first probe holder 150 defines a first slot 170, the second probe holder 152 defines a second slot 172, and the third probe holder 154 defines a third slot 174. Each of the sensor assemblies (i.e., the first sensor assembly 130, the second sensor assembly 132, and the third sensor assembly 134) may be configured to detect if an ultrasound probe (104, 105, or 106) is positioned in one of the probe holders (150, 152, 154). For example, the first sensor assembly 130 may be configured to detect if one of the ultrasound probes (104, 105, 106) is positioned in the first probe holder 150, the second sensor assembly 132 may be configured to detect if one of the ultrasound probes (104, 105, 106) is positioned in the second probe holder 152, and the third sensor assembly 134 may be configured to detect if one of the ultrasound probes (104, 105, 106) is positioned in the third probe holder 154.

Each of the ultrasound probes (104, 105, 106) may include a cable configured carry signals from the transmitter 102 and ultrasound data from the ultrasound probes (104, 105, 106). According to other embodiments, one of more of the ultrasound probes (104, 105, 106) may be wireless. Each of the sensor assemblies (130, 132, 134) may include one or more sensors capable of detecting the ultrasound probe of the passage of a cable that is part of the ultrasound probe. Each of the sensor assemblies (130, 132, 134) may include one or more sensors selected from the group including: a capacitive sensor, an electromagnetic sensor, an inductive proximity sensor, an optical sensor, or any other type of sensor configured to detect if an ultrasound probe is in one of the probe holders or if the cable has passed through a slot in the probe holder. According to an exemplary embodiment, each probe holder may include a slot for allowing passage of a cable attached to the ultrasound probe and the sensor assembly for each probe holder may be positioned to detect the passage of the probe cable through the slot. Once an association has been made between one of the ultrasound probes (104, 106, and 108) and one of the probe holders (150, 152, and 153), the processor 116 may determine if the associated ultrasound probe is in in a particular probe holder by tracking the number of times the probe cable has passed through the slot for a particular probe holder. For example, the processor 116 may track the ultrasound probe in a memory and toggle the status of the ultrasound probe between "in the ultrasound probe holder" and "out of the ultrasound probe holder." The processor 116 may be further configured to adjust a probe status based on whether the ultrasound probe is detected to be "in the ultrasound probe holder" or "out of the ultrasound probe holder." For example, the processor 116 may determine that the ultrasound probe is being used for active scanning based on whether or not the ultrasound probe is in the probe holder according to an embodiment.

The ultrasound imaging system 100 also includes a plurality of light assemblies. For example, FIG. 1 includes a first light assembly 140, a second light assembly 142, and a third light assembly 144. Each of the light assemblies (140, 142, and 144) may include one or more light-emitting diodes (LEDs), one or more organic light-emitting diodes (OLEDs), or one or more incandescent light bulbs. Each of the light assemblies is configured to selectively illuminate some or all of one of the probe holders. For example, the first light assembly 140 is configured to selectively illuminate some or all of the first probe holder 150, the second light assembly 142 is configured to selectively illuminate some or all of the second probe holder 152, and the third light assembly is configured to selectively illuminate some or all of the third probe holder 154.

According to an embodiment, each of the light assemblies (140, 142, and 144) may include to ability to provide light of two or more different colors to illuminate the respective probe holder with two or more different colors. For example, each of the light assemblies may include LEDs, OLEDs or incandescent bulbs of two or more different colors. According to another embodiment, each of the light assemblies (140, 142, and 144) may include a red element, a green element, a blue element and a white element in order to allow for the generation of any desired color by controlling the relative contributions of the red element, the green element, the blue element and a white element. According to an exemplary embodiment, each of the light assemblies (140, 142, 144) may include a red LED as the red element, a green LED as the green element, a blue LED as the blue element, and a white LED as the white element. According to another exemplary embodiment, each of the light assemblies (140, 142, 144) may include a red OLED as the red element, a green OLED as the green element, a blue OLED as the blue element, and a white OLED as the white element.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component, and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, color Doppler, M-mode, color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the image frames in real time while a procedure is being carried out on a patient. A video processor module may store the image frames in an image memory, from which the images are read and displayed.

Figure 3:
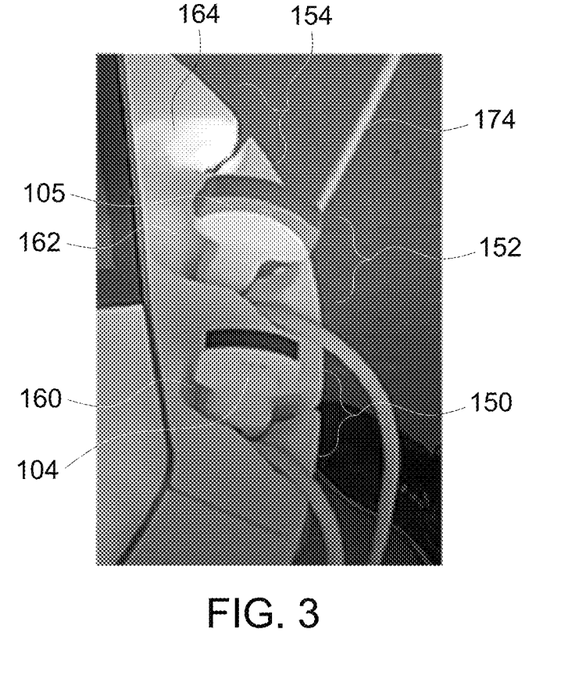
FIG. 3 is an illustration of a plurality of probe holders in accordance with an embodiment.
Figure 4:
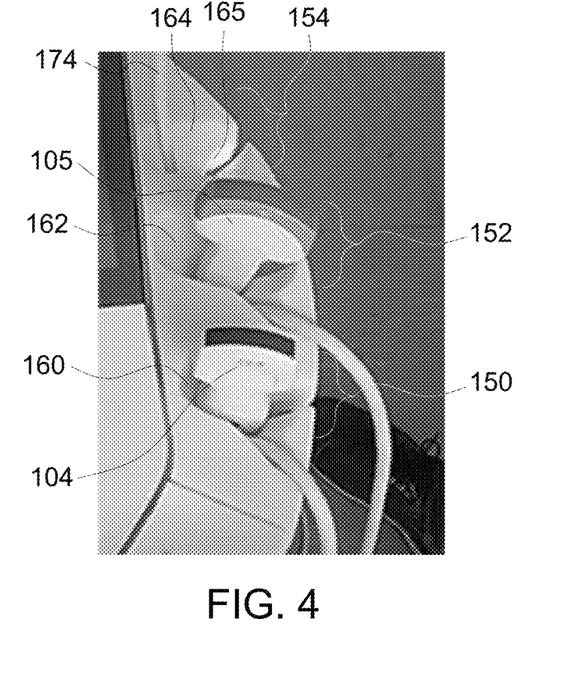
FIG. 4 is an illustration of a plurality of probe holders in accordance with an embodiment.

FIG. 3 is an illustration of the probe holders of the ultrasound imaging system 100 according to an embodiment. FIG. 4 is an illustration of the probe holders of the ultrasound imaging system 100 according to an embodiment. FIG. 3 and FIG. 4 both include the first probe holder 150, the second probe holder 152, and the third probe holder 154. FIG. 3 and FIG. 4 both show the first probe 104 in the first probe holder 150 and the second probe 105 in the second probe holder 152. A cable 174 of the third ultrasound probe 106 is shown in both FIG. 3 and FIG. 4. According to an embodiment, each of the probe holders includes a cradle for supporting the an ultrasound probe. For example, the first probe holder 150 includes a first cradle 160, the second probe holder 152 includes a second cradle 162, and the third probe holder 154 includes a third cradle 164. According to the embodiment shown in FIGS. 3 and 4, the cradle in each of the probe holders is a tapered region configured to receive the ultrasound probe. The third cradle 164 is clearly illuminated in FIG. 3. In FIG. 3, the third probe has clearly been removed from the third probe holder 154 as illustrated by the position of the cable 174 associated with the third probe 106. The first probe holder 150 and the second probe holder 152 are not illuminated in FIG. 3

FIG. 3 and FIG. 4 also demonstrate an embodiment where the sensor assemblies are used to detect the passage of the probe cable through a slot in each probe holder. For example, in FIG. 3, the probe cable 174 is outside of the third probe holder 154 and the third light assembly is actively illuminating the third probe holder 154 including the cradle 164. In FIG. 4, the probe cable 174 of the third probe 106 is clearly still in the third probe holder 154. This means that the processor 116 has not received a signal from the third sensor assembly 134 indicating that the third ultrasound probe 106 has been removed from the third probe holder 154. As a result, the processor 116 is controlling the third light assembly 144 to indicate a probe status that is different from the probe status indicated in FIG. 3. The processor 116 is controlling the third light assembly 144 to illuminate the third probe holder 154 differently than the way shown in FIG. 3. According to an embodiment, the a region of illumination 165 is smaller in FIG. 4 than in FIG. 3, where all of the visible surfaces of the cradle 164 are illuminated. In FIG. 4, only a portion of the visible surfaces of the cradle 164 are illuminated. Additionally, the third probe holder 154 may be illuminated with a different color in FIG. 4 compared to FIG. 3.

In FIG. 3, the processor 116 is controlling the plurality of light assemblies (140, 142, 144) to illuminate the third probe holder 154.

The processor 116 is configured to control the plurality of light assemblies (140, 142, and 144) in order to selectively illuminate one or more of the plurality of probe holders (150, 152, and 154). The processor 116 may be configured to control the plurality of light assemblies (140, 142, and 144) in order to illuminate one or more of the plurality of probe holders with a single color of light and/or the processor 116 may be configured to control the plurality of light assemblies (140, 142, and 144) in order to illuminate one or more of the plurality of probe holders using different colors of light.

Figure 5:
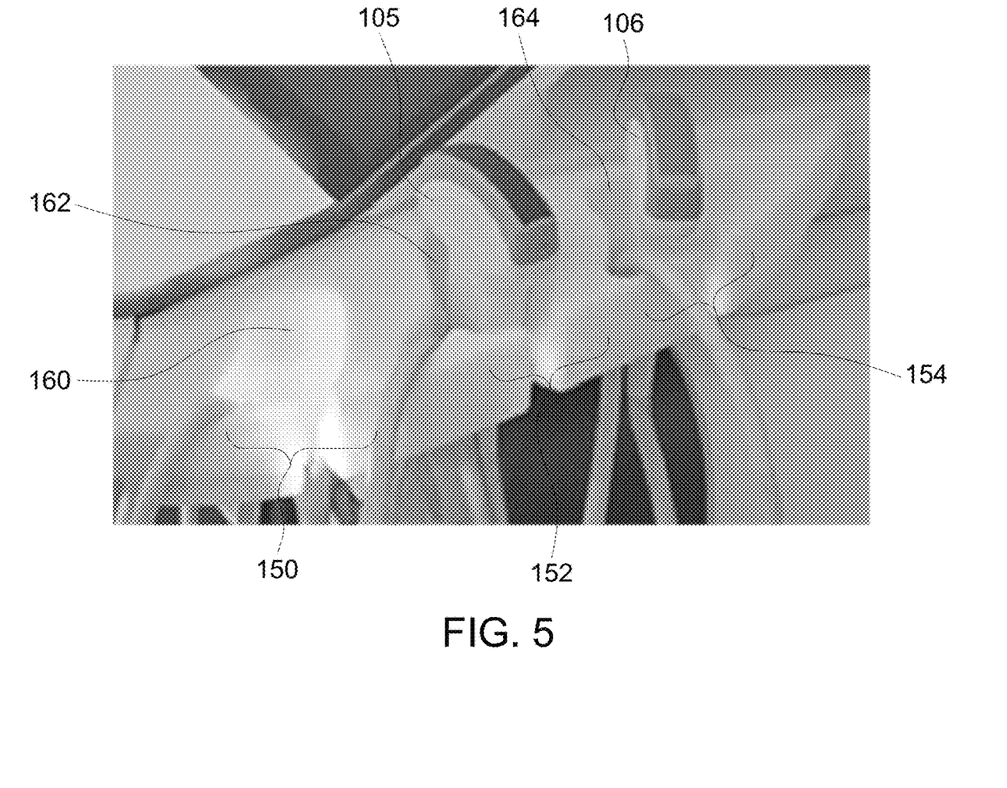
FIG. 5 is an illustration of a plurality of probe holders in accordance with an embodiment.

FIG. 5 is representation of the plurality of probe holders in accordance with an exemplary embodiment. FIG. 5 includes the first probe holder 150, the second probe holder 152, the third probe holder 154, the first cradle 160, the second cradle 162, and the third cradle 164. The first ultrasound probe has been removed from the first cradle, but the second ultrasound probe 105 and the third ultrasound probe 106 are positioned in their respective probe holders. FIG. 5 shows an example of how the first light assembly may be used to illuminate all or nearly all of the first cradle 160.

Figure 6:
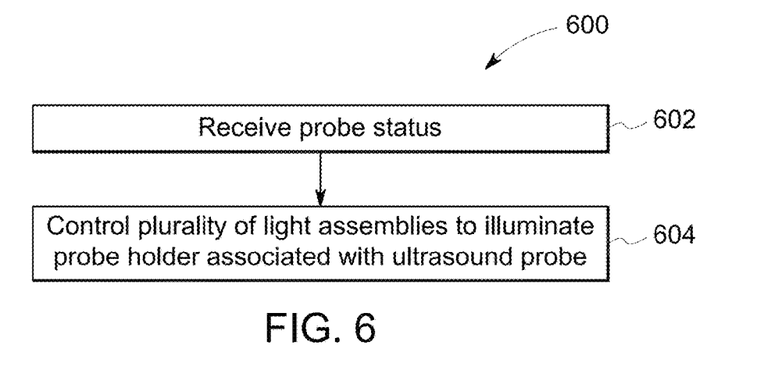
FIG. 6 is a flow chart of a method in accordance with an embodiment.

FIG. 6 is a flow chart of a method 600 in accordance with an embodiment. The method 600 may, for instance, be performed with the ultrasound imaging system 100 according to an exemplary embodiment. The individual blocks of the flow chart represent steps that may be performed in accordance with the method 600. Additional embodiments may perform the steps shown in a different sequence and/or additional embodiments may include additional steps not shown in FIG. 6. The technical effect of the method 600 is the illumination of a probe holder associated with an ultrasound probe to indicate a probe status.

At step 602, the processor 116 receives a probe status. The probe status may be one of activated, actively scanning, or inactive. The probe status may be probe diagnostics test in progress. For embodiments involving an probe diagnostics test, the probe status may additionally include passed and failed.

At step 602, the processor 116 may receive the probe status automatically, such as after the selection of a protocol, or the probe status may by manually inputted through the user input device 115.

After receiving the probe status, the method 600 advances to step 604, where the processor 116 controls the plurality of light assemblies to illuminate one of the more of the probe holders (150, 152, 154). According to an embodiment where the probe status is "activated," the processor 116 may control the plurality of light assemblies to illuminate the probe holder associated with the ultrasound probe that has been activated in order to help the clinician identify which of the plurality of ultrasound probes to use for a specific procedure. According to an embodiment where the probe status is "probe diagnostics test in progress," the processor 116 may control the plurality of light assemblies to illuminate, with a first color, the probe holder associated with the ultrasound probe undergoing the probe diagnostics test. For example, the first color may be orange. According to an embodiment, the processor 116 may control the plurality of light assemblies to illuminate the probe holder associated with the ultrasound probe with a pattern such as a flashing pattern or a strobing pattern.

The processor 116 may control the plurality of light assemblies to illuminate the probe holder associated with the ultrasound probe with a second color to indicate that the ultrasound probe has passed the probe diagnostics test or the processor 116 may control the plurality of light assemblies to illuminate the probe holder associated with the ultrasound probe with a third color to indicate that the ultrasound probe has failed the probe diagnostics test. According to an embodiment, the first color may be green to indicate the ultrasound probe has passed the probe diagnostics test and the second color may be red to indicate the ultrasound probe has failed the probe diagnostics test. Those skilled in the art should appreciate that different colors may be used according to various embodiments.

According to an embodiment, the processor 116 may receive an updated probe status after step 604. Updated probe statuses could include "inactive", and/or a different ultrasound probe could be activated. The processor 116 may be configured to illuminate one of the probe holders.

According to another embodiment the processor 116 may control the plurality of light assemblies to illuminate the probe holder associated with an ultrasound probe that has been removed from one of the probe holders (150, 152, 154) to actively scan the patient (i.e., according to an embodiment where the probe status is "actively scanning"). According to an exemplary embodiment, the processor 116 may control the plurality of light assemblies in response to receiving a signal from one of the sensor assemblies (130, 132, 134) indicating that the ultrasound probe has been removed from its respective probe holder. Illuminating the one of the plurality of probe holders (150, 152, 154) from which the ultrasound probe has been removed provides the user with a clear indication of the position to which the ultrasound probe should be returned after scanning. According to an embodiment, the processor 116 may control the plurality of light assemblies to no longer illuminate the probe holder associated with the ultrasound probe that was used to actively scan the patient after the ultrasound probe has been returned to its respective probe holder. This may also be determined based on a signal from one of the sensor assemblies (130, 132, 134). For example, if the first ultrasound probe 104 is removed from the first probe holder 150, the processor 116 may control the plurality of light assemblies to illuminate the first probe holder 150 while the first ultrasound probe 104 is being used to actively scan the patient. Then, once the first ultrasound probe 104 has been returned to the first probe holder 150, the processor 116 may control the plurality of light assemblies to no longer illuminate the first probe holder. According to anther embodiment, the processor 116 may be configured to change the color used to illuminate the first probe holder, for instance, in order to indicate that the status of the first ultrasound probe 104 is "actively scanning." According to other embodiments, the processor 116 may be configured to control the illumination of other ones of the plurality of probe holders to indicate that a different ultrasound probe is being used to actively scan the patient.

Figure 7:
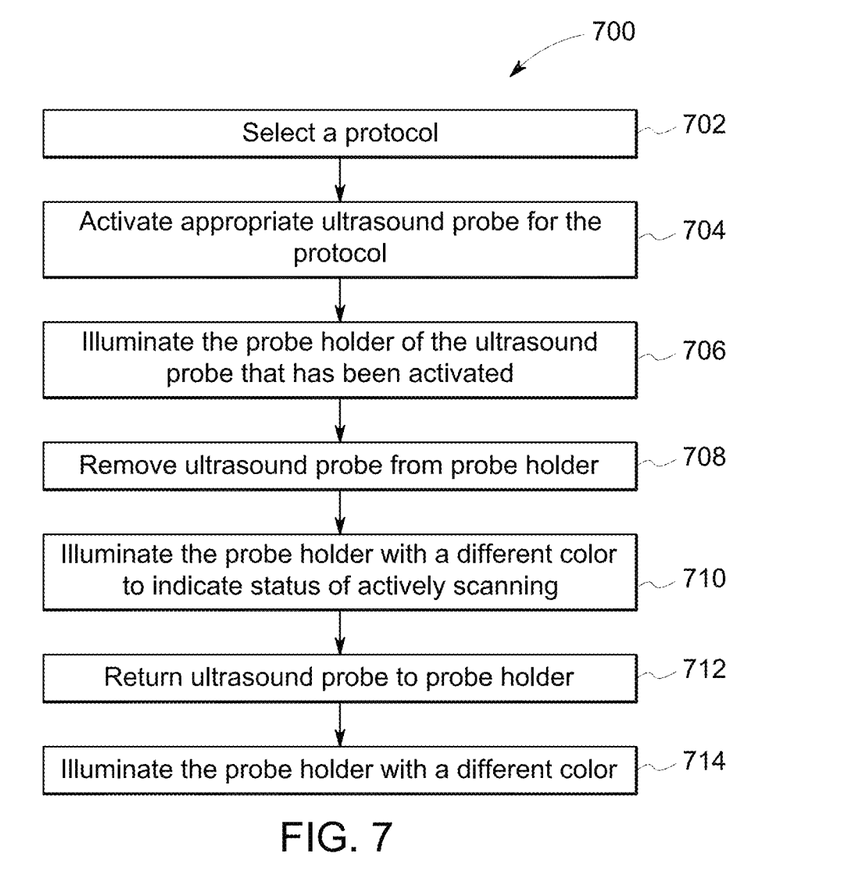
FIG. 7 is a flow chart of a method in accordance with an embodiment.

FIG. 7 is a flow chart of a method 700 in accordance with an embodiment. The method 700 may, for instance, be performed with the ultrasound imaging system 100 according to an exemplary embodiment. The individual blocks of the flow chart represent steps that may be performed in accordance with the method 700. Additional embodiments may perform the steps shown in a different sequence and/or additional embodiments may include additional steps not shown in FIG. 7. The technical effect of the method 700 is the illumination of a probe holder associated with an ultrasound probe to indicate a probe status.

At step 702, a selection of a protocol is received by the processor 116. The selection of the protocol may be in response to a input through the user input device 115, or the processor 116 may receive a selection of the protocol automatically as either a default setting for the ultrasound imaging system or for embodiments where the protocol is part of a larger workflow that was previously manually selected.

At step 704, the processor 116 activates the appropriate ultrasound probe for the selected protocol. Each protocol is ideally performed with a specific ultrasound probe or an ultrasound probe of a specific type based on factors such as the size and shape of the probe head, the type of array, the frequency of the ultrasound probe, and/or the number of elements in the array. According to an embodiment, the processor 116 may be configured to select the one of the plurality of ultrasound probes (104, 105, 106) that would be the most well-suited for the selected protocol. The method 700 will be described hereinafter with respect to an embodiment where the first ultrasound probe 104 is the most appropriate for the selected protocol, but according to other embodiments, the second ultrasound probe 105, the third ultrasound probe 106 or an additional ultrasound probe not shown in FIG. 2 may be the most appropriate for the selected protocol.

As discussed hereinabove, each of the ultrasound probes (104, 105, 106) is associated with one of the plurality of probe holders (150, 152, 154). According to the embodiment shown in FIG. 2, the first ultrasound probe 104 is associated with the first probe holder 150, the second ultrasound probe 105 is associated with the second probe holder 152, and the third ultrasound probe 106 is associated with the third probe holder 154. However, it should be noted that it is possible for the user to change the associations between the various ultrasound probes (104, 105, 106) and the various probe holders (150, 152, 154).

At step 706, the processor 116 controls the plurality of light assemblies to illuminate the probe holder associated with the appropriate ultrasound probe. As discussed above, for an embodiment where the first ultrasound probe 104 is the appropriate ultrasound probe and the first ultrasound probe is associated with the first probe holder 150, the processor 116 will control the plurality of light assemblies to illuminate the first probe holder 150 with a first color. According to an embodiment, the first color may be red. The first color may be any other color according to various embodiments. Due to the illumination of the first probe holder 150, it is very easy for the clinician to see the location of the appropriate ultrasound probe for the current protocol.

At step 708, the clinician removes the first ultrasound probe 104 from the first ultrasound probe holder 150. The processor 116 receives a signal from the first sensor assembly 130 in response to the clinician removing the first ultrasound probe 104 from the first ultrasound probe holder 150. After receiving the signal from the first sensor assembly 130, at step 710, the processor 116 controls the plurality of light assemblies (140, 142, 144) to illuminate the first probe holder 150 with a second color that is different than the first color to indicate that the clinician is actively scanning with the first ultrasound probe 104. According to an exemplary embodiment, the second color may be green to indicate that the first ultrasound probe 104 is being used for scanning.

After completing the scanning of the patient, the clinician returns the first ultrasound probe 104 to the first probe holder 150 at step 712. In response to receiving a signal from the first sensor assembly 130 indicating that the first ultrasound probe 104 has been returned to the first probe holder 104, at step 714, the processor 116 controls the plurality of light assemblies to illuminate the first probe holder 150 with the first color to indicate that the first ultrasound probe 104 is still active, but that it is not being used for active scanning. According to other embodiments, the processor 116 may be configured to turn off the illumination for the first probe holder after the clinician returns the first ultrasound probe 104 to the first probe holder 150.

Figure 8:
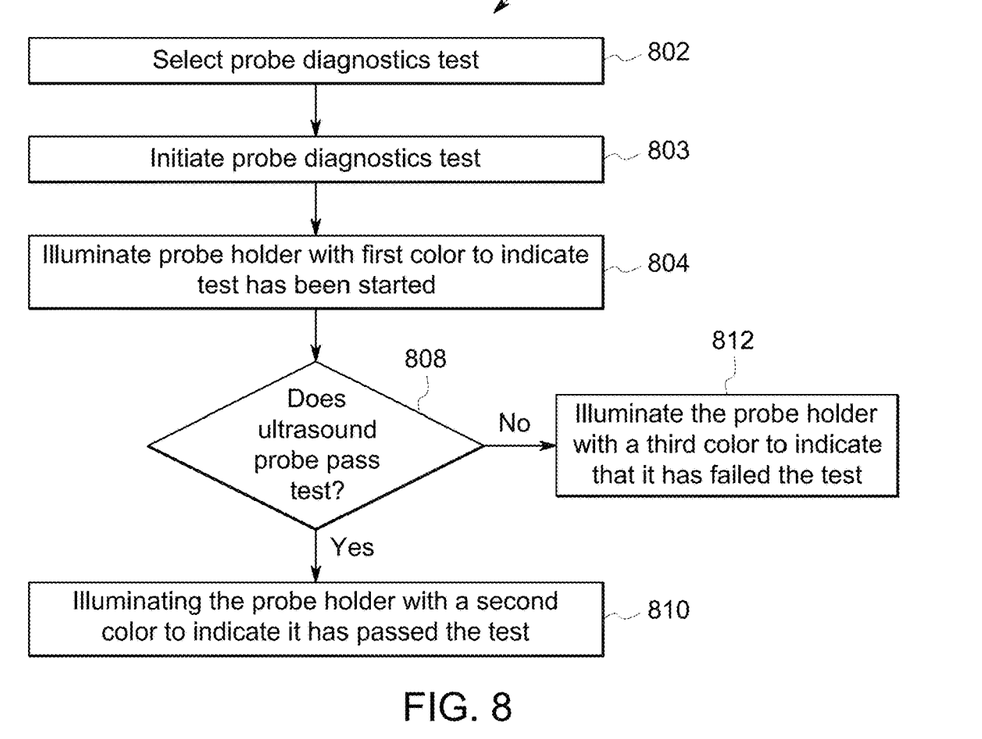
FIG. 8 is a flow chart of a method in accordance with an embodiment.

FIG. 8 is a flow chart of a method 800 in accordance with an embodiment. The method 800 may, for instance, be performed with the ultrasound imaging system 100 according to an exemplary embodiment. The individual blocks of the flow chart represent steps that may be performed in accordance with the method 800. Additional embodiments may perform the steps shown in a different sequence and/or additional embodiments may include additional steps not shown in FIG. 8. The technical effect of the method 800 is the illumination of a probe holder associated with an ultrasound probe to indicate a probe status.

At step 802, the processor 116 receives a selection of a probe diagnostics test. According to an embodiment, the processor 116 may be configured to receive the selection of the test automatically or in response to receiving an input through the user input device 115. According to some embodiments, the processor 116 may be configured to automatically initiate the probe diagnostics test after a predetermined amount of time, a predetermined number of scans, or every time the ultrasound imaging system is turned on.

At step 803, the processor 116 is configured to initiate the probe diagnostics test in response to receiving the selection of the probe diagnostics test at step 802.

At step 804, the processor 116 is configured to control the plurality of light assemblies to illuminate the one of the plurality of probe holders (150, 152, 154) associated with the ultrasound probe being tested. The method 800 will be described according to an embodiment where the probe diagnostics test is being performed on the second probe 105 that is associated with the second probe holder 152. Therefore, according to an exemplary embodiment, at step 804, the processor 116 is configured to control the plurality of light assemblies to illuminate the second probe holder 152 with a first color at step 804. According to an embodiment, the first color may be orange. The first color may be any other color according to various embodiments. The processor 116 may further control the plurality of light assemblies to illuminate the second probe holder 152 in a flashing or strobing pattern to indicate that the probe diagnostics test is being performed.

At step 808, the method 800 advances to step 810 if the second ultrasound probe 105 passes the probe diagnostics test and the method 800 advances to step 812 if the second ultrasound probe 105 fails the probe diagnostics test.

At step 810, the processor 116 controls the plurality of light assemblies to illuminate the second probe holder 152 with a second color to indicate that the second ultrasound probe 105 passed the probe diagnostics test. According to an embodiment, the second color may be green to indicate that the second ultrasound probe 105 passed the probe diagnostics test. The second color may be any other color according to various embodiments.

At step 812, the processor 116 controls the plurality of light assemblies to illuminate the second probe holder 152 with a third color to indicate that the second ultrasound probe 105 failed the probe diagnostics test. According to an embodiment, the third color may be red to indicate that the second ultrasound probe 105 failed the probe diagnostics test. The third color may be any other color according to various embodiments.

While the method 800 was described according to an embodiment where the probe diagnostics test was performed on the second ultrasound probe 105, it should be appreciated that the method 800 may be performed on any of the ultrasound probes, including the first ultrasound probe 104 or the second ultrasound probe 105. For embodiments where the probe diagnostics test is performed on the first ultrasound probe 104, the processor 116 will control the illumination of the first probe holder 150. For embodiments where the probe diagnostics test is performed on the third ultrasound probe 104, the processor 116 will control the illumination of the third probe holder 154. Additionally, it should be appreciated that different colors may be used for the first color, the second color, and/or the third color according to various embodiments.

Figure 9:
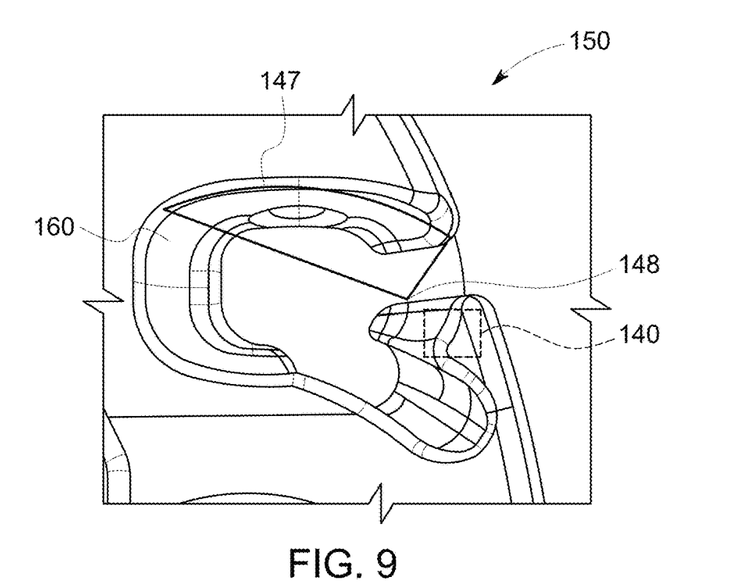
FIG. 9 is an illustration of a probe holder in accordance with an exemplary embodiment.

FIG. 9 is an illustration showing a more detailed view of the first probe holder 150 in accordance with an embodiment. The first probe holder 150 includes the first cradle 160, and a representation of the first light assembly 140 is shown with dashed lines since it is located underneath the outer surface of the probe holder 150 shown in FIG. 9. FIG. 9 includes an optical window 148 through which light from one or more LEDs is emitted. FIG. 9 also includes a representation of light 147 emitted from the optical window 148. The representation of light 147 shows the portion of the cradle 160 that is directly illuminated with the light from the first light assembly 140. According to an exemplary embodiment, the light is reflected to illuminate all or nearly all of the first cradle 160. According to other embodiments, some or all of the first probe cradle 160 and/or some or all of the probe holder 150 may be constructed with a transparent or semitransparent material. According to these embodiments, the first light assembly 140 (located inside the first probe holder 150) may generate light that is visible through the transparent or semitransparent material used for some or all of the probe holder 150. FIG. 9 is just one exemplary embodiment and other configurations may be used to illuminate one or more of the probe holders.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An ultrasound imaging system comprising:
   a plurality of probe holders;
   a plurality of light assemblies attached to the plurality of probe holders, wherein each of the plurality of light assemblies is configured to selectively illuminate a different one of the plurality of probe holders; and
   a processor connected to the plurality of light assemblies, wherein the processor is configured to control the plurality of light assemblies in order to selectively illuminate one or more of the plurality of probe holders in order to convey a probe status.

2. The ultrasound imaging system of claim 1, wherein each of the plurality of probe holders further comprises a slot for allowing passage of a cable of an ultrasound probe, and further comprising a plurality of sensor assemblies attached to the plurality of probe holders, wherein each of the plurality of sensor assemblies is configured to detect movement of the cable through the slot of one of the plurality of probe holders.

3. The ultrasound imaging system of claim 2, wherein the processor is configured to control the plurality of light assemblies to illuminate the one of the plurality of probe holders in response to detecting a signal from one of the plurality of sensor assemblies indicating that the ultrasound probe has been removed from the one of the plurality of probe holders.

4. The ultrasound imaging system of claim 2, wherein the processor is configured to control the plurality of light assemblies to illuminate one of the plurality of probe holders with a first color to indicate that the ultrasound probe has been removed from the one of the plurality of probe holders and with a second color to indicate that the ultrasound probe has been returned to the one of the plurality of probe holders in response to receiving signals from one of the plurality of sensor assemblies.

5. The ultrasound imaging system of claim 1, wherein the processor is configured to control the plurality of light assemblies to illuminate one of the plurality of probe holders with a first color to indicate that an ultrasound probe associated with the one of the plurality of probe holders has been activated.

6. The ultrasound imaging system of claim 5, wherein the processor is configured to control the plurality of light assemblies to illuminate the one of the plurality of probe holders with a second color, different than the first color, to indicate that the ultrasound probe is currently being used for scanning.

7. The ultrasound imaging system of claim 1, wherein the processor is configured to control the plurality of light assemblies to illuminate one of the plurality of probe holders to indicate a status of a probe diagnostics test being performed on an ultrasound probe associated with the one of the plurality of probe holders.

8. The ultrasound imaging system of claim 7, wherein the processor is configured to:
control the plurality of light assemblies to illuminate the one of the plurality of probe holders with a first color to indicate that the probe diagnostics test is being performed on the ultrasound probe;
illuminate the one of the plurality of probe holders with a second color to indicate that the ultrasound probe has passed the probe diagnostics test; and
illuminate the one of the plurality of probe holders with a third color to indicate that the ultrasound probe has failed the probe diagnostics test.

9. The ultrasound imaging system of claim 1, wherein the probe cradle is made of a transparent material or a semi-transparent material and the LED is positioned inside the cradle, and wherein light from the LED is visible from outside the probe cradle.

10. The ultrasound imaging system of claim 1, further comprising a plurality of ultrasound probes, each associated with a different one of the plurality of probe holders, and wherein the processor is configured to control the plurality of light assemblies to illuminate the plurality of probe holders in order to indicate one of the plurality of ultrasound probes for a selected protocol.

11. The ultrasound imaging system of claim 1, further comprising a plurality of ultrasound probes, each associated with a different one of the plurality of probe holders, and wherein the processor is configured to control the plurality of light assemblies to illuminate one of the plurality of probe holders while one of the plurality of ultrasound probes associated with the one of the plurality of probe holders is being used for scanning.

12. A method for use with an ultrasound imaging system including a plurality of probe holders and a plurality of ultrasound probes, where each of the plurality of ultrasound probes is associated with a different one of the plurality of probe holders, and a plurality of light assemblies attached to the plurality of probe holders, the method comprising:
receiving a probe status with respect to one of the plurality of ultrasound probes; and
controlling, with a processor, the plurality of light assemblies in order to illuminate all of a respective cradle of the one of the plurality of probe holders associated with the one of the plurality of ultrasound probes in order to convey the probe status.

13. The method of claim 12, wherein the probe status is selected from the group consisting of activated and actively scanning.

14. The method of claim 12, further comprising receiving an updated probe status; and controlling, with the processor, the plurality of light assemblies in order to illuminate all of the respective cradle of the one of the plurality of probe holders with a different color to convey the updated probe status.

15. The method of claim 14, wherein the probe status is activated and the updated probe status is actively scanning.

16. The method of claim 12, further comprising receiving an updated probe status; and controlling, with the processor, the plurality of light assemblies in order to not illuminate the one of the plurality of probe holders associated with the one of the plurality of ultrasound probes to convey the updated probe status.

17. The method of claim 16, wherein the probe status is actively scanning and the updated probe status is inactive.

18. The method of claim 12, wherein the probe status is probe diagnostics test in progress.

* * * * *